United States Patent
Braun et al.

(10) Patent No.: US 7,531,502 B2
(45) Date of Patent: May 12, 2009

(54) DIAGNOSTIC CONJUGATE USEFUL FOR INTRACELLULAR IMAGING AND FOR DIFFERENTIATING BETWEEN TUMOR- AND NON-TUMOR CELLS

(75) Inventors: Klaus Braun, Sandhausen (DE); Jürgen Debus, Stettfeld (DE); Jürgen Jenne, Mannheim (DE); Rüdiger Pipkorn, Heidelberg (DE); Ralf Rastert, Mosbach (DE); Waldemar Waldeck, Laudenbach (DE); Isabell Braun, Cölbe-Bürgeln (DE); Stefan Heckl, Heidelberg (DE)

(73) Assignee: Deutsches Krebsforschungszentrum Stiftung Des Offentlichen Rechts (DE)

( * ) Notice: Subject to any disclaimer, the term of this patent is extended or adjusted under 35 U.S.C. 154(b) by 470 days.

(21) Appl. No.: 10/502,442

(22) PCT Filed: Jan. 22, 2003

(86) PCT No.: PCT/EP03/00609

§ 371 (c)(1),
(2), (4) Date: Oct. 4, 2004

(87) PCT Pub. No.: WO03/061712

PCT Pub. Date: Jul. 31, 2003

(65) Prior Publication Data

US 2006/0019249 A1 Jan. 26, 2006

(30) Foreign Application Priority Data

Jan. 22, 2002 (EP) ................................. 02001506

(51) Int. Cl.
*A01N 37/18* (2006.01)
*A61K 38/16* (2006.01)
*A61K 38/00* (2006.01)
*A61K 38/04* (2006.01)
*C07K 7/00* (2006.01)
*C07K 17/00* (2006.01)

(52) U.S. Cl. .................. 514/2; 514/8; 514/12; 514/21; 530/324; 530/326

(58) Field of Classification Search ........................ None
See application file for complete search history.

(56) References Cited

U.S. PATENT DOCUMENTS 6,821,948 B1 * 11/2004 Braun et al. .................. 514/2
2006/0074034 A1 * 4/2006 Collins et al. ................. 514/44

FOREIGN PATENT DOCUMENTS

WO WO 03/061712 A1 1/2003

OTHER PUBLICATIONS

Caravan, et al., Gadolinium(III) Chelates as MRI Contrast Agents: Structure, Dynamics, and Applications. Chem Rev. Sep. 8, 1999;99(9):2293-352.*
Biochemistry John Wiley and Sons, 1990, p. 126-129.*
Schiavone N et al., Antisense oligonucleotide drug design.Curr Pharm Des. 2004;10(7):769-84.*
Braun et al., A biological transporter for the delivery of peptide nucleic acids (PNAs) to the nuclear compartment of living cells.J Mol Biol. Apr. 26, 2002;318(2):237-43.*
Berger, et al., "Recent advances in imaging endogenous or transferred gene expression utilizing radionuclide . . . " Breast Cancer Research, 2001, vol. 3, pp. 28-35.
Heckl, et al., "CNN-Gd3+ Enables Cell Nucleus Molecular Imaging of Prostate Cancer Cells: The Last 600 nm", Cancer Research, 2002, vol. 2, pp. 7018-7024.
R.B. Merrifield, "The Synthesis of a Tetrapeptide", Journal of American Chemical Society, 1963, vol. 85, pp. 2149-2154.
Carpino, et al., "The 9-Fluorenylmethoxycarbonyl Amino-Protecting Group", Journal of Organic Chemistry, 1972, vol. 37, pp. 3404-3409.
Slamon, et al., "Use of Chemotherapy Plus a Monclonial Antibody Against Her2 for Metastatic Breast . . . ", The New England Journal of Medicine, 2001, vol. 344, pp. 783-788.
Pooga, et al., "Cell Penetration by Transportan", The FASEB Journal, 1998, vol. 12, pp. 67-77.
Derossi, et al., "Trojan peptides: the penetratin system for intracellular delivery", Trends in Cell Biology, 1998, vol. 8, pp. 84-87.

* cited by examiner

*Primary Examiner*—Michael Burkhart
*Assistant Examiner*—Maria Leavitt
(74) *Attorney, Agent, or Firm*—Kelly Reynolds; Intellectual Property/Technology Law; Steven J. Hulquist

(57) ABSTRACT

Described is a diagnostic conjugate comprising (a) a transmembrane module (TPU), (b) an address module (AS), preferably an antisense peptide nucleic acid (PNA), and (c) a signaling module (SM). The conjugate is useful for intracellular imaging, preferably via MRI, and, e.g., for differentiating between tumor- and non-tumor cells.

16 Claims, 5 Drawing Sheets

Fig. 2. Confocal laser scanning microscopy (CLSM) of human HeLa cervix carcinoma cells. Cytoplasm directed ACGT {$Gd^{3+}$-DTPH-Lys-Lys-[AS]-Cys-constructs (100 pM, FITC labeled)} (#153c, Table 1). After 1 h incubation, fluorescence signals were only detected within the cytoplasm, whereas the nuclei remained unstained.

a.)   b)   c.)

C-myc DNA (oncogene)

AC X00364

| | | | | | | |
|---|---|---|---|---|---|---|
| TTTAGGGGAT | AGCTCTGCAA | GGGGAGAGGT | TCGGGACTGT | GGCGCGCACT | GCGCGCTGCG | 4440 |
| CCAGGTTTCC | GCACCAAGAC | CCCTTTAACT | CAAGACTGCC | TCCCGCTTTG | TGTGCCCCGC | 4500 |
| TCCAGCAGCC | TCCCGCGACG | ATGCCCCTCA | ACGTTAGCTT | CACCAACAGG | AACTATGACC | 4560 |
| TCGACTACGA | CTCGGTGCAG | CCGTATTTCT | ACTGCGACGA | GGAGGAGAAC | TTCTACCAGC | 4620 |
| AGCAGCAGCA | GAGCGAGCTG | GAGCCCCGG | CGCCAGCGA | GGATATCTGG | AAGAAATTCG | 4680 |
| AGCTGCTGCC | CACCCCGCCC | GTGTCCCCTA | GCCGCCGCTC | CGGGCTCTGC | TCGCCCTCCT | 4740 |
| ACGTTGCGGT | CACACCCTTC | TCCCTTCGGG | GAGACAACGA | CGGCGGTGGC | GGGAGCTTCT | 4800 |
| CCACGGCCGA | CCAGCTGGAG | ATGGTGACCG | AGCTGCTGGG | AGGAGACATG | GTGAACCAGA | 4860 |
| GTTTCATCTG | CGACCCGGAC | GACGAGACCT | TCATCAAAAA | CATCATCATC | CAGGACTGTA | 4920 |
| TGTGGAGCGG | CTTCTCGGCC | GCTGCCAAGC | TCGTCTCAGA | GAAGCTGGCC | TCCTACCAGG | 4980 |
| CTGCGCGCAA | AGACAGCGGC | AGCCCGAACC | CCGCCCGCGG | CCACAGCGTC | TGCTCCACCT | 5040 |
| CCAGCTTGTA | CCTGCAGGAT | CTGAGCGCCG | CCGCCTCAGA | GTGCATCGAC | CCCTCGGTGG | 5100 |
| TCTTCCCCTA | CCCTCTCAAC | GACAGCAGCT | CGCCCAAGTC | CTGCGCCTCG | CAAGACTCCA | 5160 |
| GCGCCTTCTC | TCCGTCCTCG | GATTCTCTGC | TCTCCTCGAC | GGAGTCCTCC | CCGCAGGGCA | 5220 |
| GCCCCGAGCC | CCTGGTGCTC | CATGAGGAGA | CACCGCCCAC | CACCAGCAGC | GACTCTGGTA | 5280 |
| AGCGAAGCCC | GCCCAGGCCT | GTCAAAAGTG | GGCGGCTGGA | TACCTTTCCC | ATTTTCATTG | 5340 |
| GCAGCTTATT | TAACGGGCCA | CTCTTATTAG | GAAGGAGAGA | TAGCAGATCT | GGAGAGATTT | 5400 |

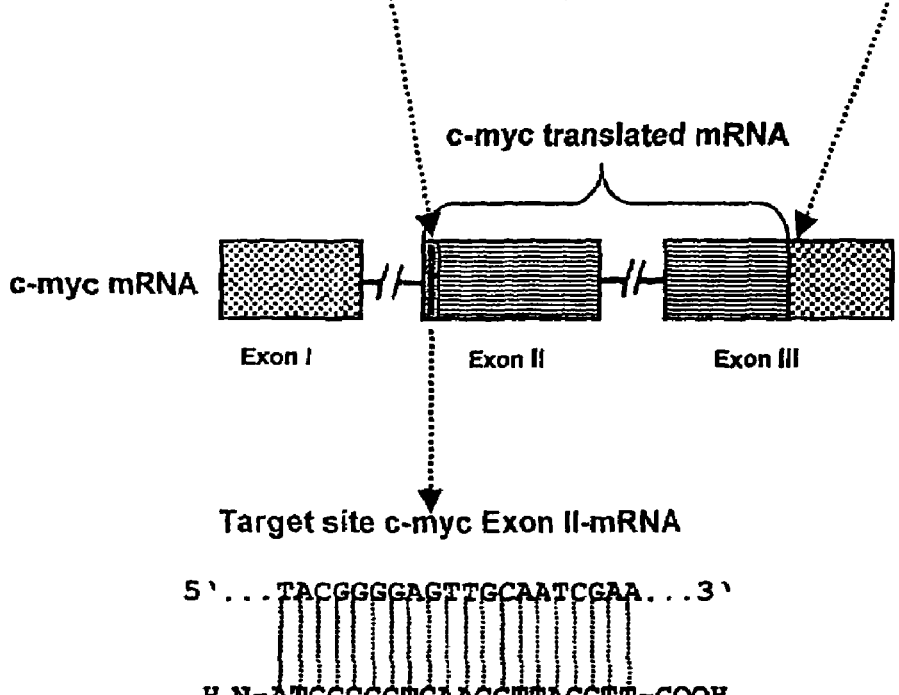

Peptide Nucleic Acid complementary sequence (antisense)

Fig 4. C-myc$_{hum}$ DNA$_{Exon\ II}$ and the complete c-myc mRNA. Exact location at which the ACGT is targeted (green). Exon I untranslated (blue hatched, Exon II translated (red), Exon III partially translated (red and blue hatched)

DIAGNOSTIC CONJUGATE USEFUL FOR INTRACELLULAR IMAGING AND FOR DIFFERENTIATING BETWEEN TUMOR- AND NON-TUMOR CELLS

CROSS-REFERENCE TO RELATED APPLICATIONS

This application is filed under the provisions of 35 U.S.C. §371 and claims the priority of International Patent Application No. PCT/EP03/00609 filed Jan. 22, 2003, which in turn claims priority of European Patent Application No. 02001506.1 filed on Jan. 22, 2002.

FILED OF THE INVENTION

The present invention relates to a diagnostic conjugate comprising (a) a transmembrane module (TPU), (b) an address module (AS), preferably an antisense peptide nucleic acid (PNA), and (c) a signalling module (SM). Said conjugate is useful for intracellular imaging, preferably via MRI, and, e.g., for differentiating between tumor- and non-tumor cells.

BACKGROUND OF THE INVENTION

Advances in MRI using the contrast agent Gadolinium (Gd) have led to a greatly enhanced precision in diagnostics. It has not yet been possible to depict the cell itself due to the extracellular distribution characteristics of the commonly used Gadolinium contrast agents. The intensively discussed and investigated Molecular Imaging methods could open the door to imaging at the cellular level.

In order to depict the cell, a contrast agent is required which can pass into the intracellular space. There have been numerous proposals as to how this could be achieved: It was attempted to achieve an optimal uptake of iron in the cell using a conventional non-viral transfection method to promote the expression of the transferrin receptor.

The gene for the transferrin receptor was transfered with the help of an adenovirus. However, it became apparent that the cells which overexpressed the transferrin receptor protected themselves from excess iron concentrations via an mRNA-mediated negative feedback inhibition of the transferrin-receptor causing decreased iron influx. This problem was overcome using ETfR (Engineered Transferrin Receptor) and MIONs (Micro Iron Oxide Nanoparticles). This process is based on liquid-phase-endocytosis of dextrane-coated MIONs via the transferrin receptor.

A further potentially attractive method for molecular imaging is the use of Gadolinium complexes (Magnevist® Schering). It has been shown that the commonly used contrast agent Magnevist® is very well suited to the display of the intercellular space, but is not suitable for intracellular imaging.

Micro-injection methods were used in *Xenopus Laevis* embryos (2-cell stadium) in order to accumulate gadolinium successfully in the intracellular space. One group attempted to accumulate a Gd-complex in the cell utilising high extracellular concentrations of a Gadolinium-complex (1-25 mg/ml) in which maximal intracellular concentrations were attained after 100 hours. With the help of a viral transporter (HIV-1 tat-peptide) high intracellular concentrations of gadolinium and iron oxide nanoparticles were achieved. Another group has even identified the HIV-1 tat peptide in the cell nucleus. There are, however, still open questions as to the transactivating effects of the viral transporter HIV-1 tat peptide in the nucleus such as the induction of apoptosis in hippocampal neurons. To summarize, there are serious disadvantages of the previous approaches, e.g., the incubation time for, e.g., the Gadolinium-complex is far too long and the concentration of this complex that has to be used is extremely high resulting in serious side effects. Moreover, despite the advances in cellular transport, there remains the question of cell specificity, i.e. all the above mentioned methods have one problem in common: they cannot differentiate between tumor and non-tumor cells.

Therefore, it is the object of the present invention to provide a diagnostic means which overcomes the disadvantages of the diagnostic tools of the prior art, i.e. which allows the fast and precise non-invasive determination, preferably the molecular imaging, of gene expression pattern in cells of a patient.

SUMMARY OF THE INVENTION

According to the invention this is achieved by the subject matters defined in the claims. The present invention provides a diagnostic conjugate comprising (a) a transmembrane module (TPU), (b) an addressing module (AS), preferably an antisense peptide nucleic acid (PNA), and (c) a signalling module (SM) allowing to determine, e.g. by MRI, the expression profile of genes of interest, e.g. genes the expression of which differs between tumor cells and non tumor cells. In the experiments leading to the present invention, the intracellular uptake of the commonly used interstitial contrast agent gadolinium was improved by building an Antisense-Conjugated-Gadolinium-Transporter (ACGT) consisting of a transmembrane transport module (TPU), an address module (c-myc mRNA directed antisense-sequence) and the $Gd^{3+}$ complex module. The so-called antisense-principle was used to realize a differentiation between tumor and non-tumor cells in MRI. Based on the differing gene expression patterns seen in tumor cells as compared to normal cells, the target-specific Antisense-Conjugated-Gadolinium-Transporter (ACGT) containing an antisense-sequence (Antisense=AS; Table 1) which is covalently bound to a transport-peptide (TPU) of human origin, and thus does not have any effect on transactivating properties was highly useful. The virtually peptidase- und nuclease resistant modified oligonucleotides (PNAS) are complementary sequences which are bound to the Gd-transporter-complex targeted at c-myc mRNA. Upon contact of the antisense-conjugated-gadolinium-transporter (ACGT) containing c-myc-targeted peptide nucleic acids (PNAs) with c-myc mRNA in the cytoplasm, a hybrid is formed composed of PNA and RNA. This hybrid begins to be slowly enzymatically cleaved after 24 hours and the ACGT then starts to leave the cell, effectively causing a delayed efflux. In cells in which c-myc mRNA is hardly present (lymphocytes and other normal cells) there is no detectable hybridization, the efflux process is immediately initiated and causes a more rapid reduction in intracellular Gd-complex concentration. Using Magnet Resonance Imaging (MRI), Gadolinium was detected within HeLa cervix-carcinoma cells as well as non-tumor cells (lymphocytes) already after 10 minutes. The ACG-Transporter was rapidly released from non-tumor cells, whereas, in HeLa cells, only a minimal efflux was observed. This suffices for a clear differentiation between tumor and non-tumor cells.

Accordingly, the present invention relates to a diagnostic conjugate comprising (a) a transmembrane module (TPU), (b) an address module (AS), and (c) a signalling module (SM).

The transport mediator for the cell membrane (=transmembrane module (TPU)) is a peptide or polypeptide which can penetrate the plasma membrane. The length of this peptide or polypeptide is not subject to any limitation as long as it has the above property. Examples of TPUs are derived preferably from the penetratin family (Derossi et al., Trends Cell Biol. 8: 84-87, 1998) or are transportan or parts thereof (Pooga et. al., The Faseb Journal 12: 68, 1998), those of the penetratin family being preferred.

In a preferred embodiment, the tranmembrane module is a human transmembrane peptide, preferably comprising one of the following amino acid sequences: KMTRQTW-WHRIKHKC (SEQ ID NO: 2); MTRQTFWHRIKHKC (SEQ ID NO: 3) or KHKIRHWFTQRTMC (SEQ ID NO: 4) (Proteindatenbank).

The transmembrane module (TPU) is produced biologically (purification of natural transmembrane peptides or fragments thereof, or cloning and expression of the sequence in a eukaryotic or prokaryotic expression system), preferably synthetically, e.g., according to the well established "Merrifield method" (Merrifield, J. Am. Chem. Soc. 85: 2149, 1963).

The selection of the address module (AM) depends on the nature of the molecules to be detected which can be, e.g., proteins or mRNAs and the person skilled in the art can easily select suitable address modules. The address module may be a nucleic acid, a protein or peptide, a chemical substance etc. Suitable address modules comprise, e.g., antibodies or fragments thereof, other ligands for proteins, e.g. ligands to receptors, or antisense RNAs with antisense nucleic acids (PNAs) which have already been discussed above being preferred. Methods for isolating and/or synthesising suitable address modules are well known to the person skilled in the art and described in standard literature and text books.

In a preferred embodiment, the peptide nucleic acid (PNA) of the diagnostic conjugate of the present invention is capable of hybridizing with an mRNA the expression or mis-expression of which is associated with a disease. Examples of diseases that can be diagnosed by use of the conjugate of the present invention are those being characterized by a modified gene expression pattern, with tumors being preferred. For the diagnosis of tumors PNAs are useful specifically hybridizing to mRNAs like c-myc- (Waardenburg et al., Anticancer Res. 18, pp. 91-95 (1998); lung and prostate tumors), c-ras-, her-(Siamon et al., New England J. Medicine 344, 783-791 (2001), breast tumors), sst1- or sst2-mRNA (Balon et al., J. Nucl. Medic. 42, 1134-1138 (2001), brain tumors).

In a more preferred embodiment, the peptide nucleic acid (PNA) of the diagnostic conjugate of the present invention is capable of hybridizing with a region of Exon II of the c-myc-mRNA and comprises the sequence $H_2N$-ATGCCCCT-CAACGTTAGCTT-COOH (SEQ ID NO: 5).

The signalling module (SM) is not subject to limitations. It can be choosen freely, depending on the effect which shall be produced in a cell. The nature of the signalling module depends on the desired diagnostic application which might be, e.g., in the field of nuclear medicine, MRT, MRS, ultrasonication or which might be based on optical methods, SPECT, PET or y camera. The person skilled in the art knows suitable signalling modules suitable for particular applications.

In a preferred embodiment, the signalling module (SM) is Gd, Fe or F. Preferably, said atoms or ions are linked to the address module as a chelate complex using, e.g., as the chelating agent diethylenetriaminepentaacetic acid (DTPA) as described in the Examples below. It could be shown previously, that in addition to Gd, Fe, e.g. ferric oxide nanoparticles (MIONs) or dextrane-coated magnetic beads trapped are useful for MR imaging.

The conjugate of the present invention, preferably contains (a) spacer(s) which is (are) preferably located between the transmembrane module (TPU) and the address module (AS) and/or the address modul (AS) and the signalling module (SM). The spacer serves for eliminating or positively influencing optionally existing steric hindrances between the modules and/or allows to separate modules from each other, e.g., in the cytoplasma of a cell.

In a preferred embodiment, the transmembrane module (TPU) of the diagnostic conjugate of the present invention is coupled to the address module (AS) via a covalently cleavable spacer I and/or the address module (AS) is coupled to the signalling module (SM) or a compound trapping the signalling module (SM) via a covalently non-cleavable spacer II.

In a more preferred embodiment, spacer I comprises a redox cleavage site, e.g. a disulfide bridge (-cysteine-S—S-cysteine-O—N—H—). The binding formed between the transmembrane module (TPU) and address module (AS) is a redox coupling (mild cell-immanent bond by means of DMSO; Rietsch and Beckwith, 1988, Ann. Rev. Gent 32: 163-184):

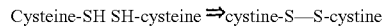

Cysteine-SH SH-cysteine ⇒cystine-S—S-cystine

The coupling of the constituents thereto is made by covalent chemical binding. The redox cleavage site is inserted chemically between TPU and AS by the above mentioned redox coupling. There is also a covalent bond, preferably an acid amide bond, between the optionally present spacer(s) and the module(s) of the conjugate. Possible alternatives are ether or ester bonds, depending on the functional group(s) present in the substance to be conjugated.

In an even more preferred embodiment, spacer II of the diagnostic conjugate is polylysine.

The address module (AS), signalling modul (SM) and or spacer II may optionally be labelled, e.g., radioactively, with a dye, with biotin/avidin, etc. Preferably, spacer II carries an FITC-label.

The most preferred embodiment of the diagnostic conjugate of the present invention has the following structure: transmembrane module (TPU)—spacer I comprising a cleavable disulfide bridge—address module (AS)—spacer II—signalling module (SM) or compound trapping the signalling module (SM).

The present invention also relates to a diagnostic composition containing a diagnostic conjugate of the present invention as well as various uses of said diagnostic conjugate. A preferred use is the selective detection of tumor cells, e.g. by MRI, using as contrast agent Gd as signalling module (SM).

BRIEF DESCRIPTION OF THE DRAWINGS

FIG. 2: Confocal laser scanning microscopy (CLSM) of human HeLa cervix carcinoma cells.

Cytoplasm directed ACGT {$Gd^{3+}$-DTPH-Lys-Lys-[AS]-Cys-constructs (100 pM, FITC labeled)} (#153c, Table 1). After 1 h incubation, fluorescence signals were only detected within the cytoplasm, whereas the nuclei remained unstained.

Figure 3:
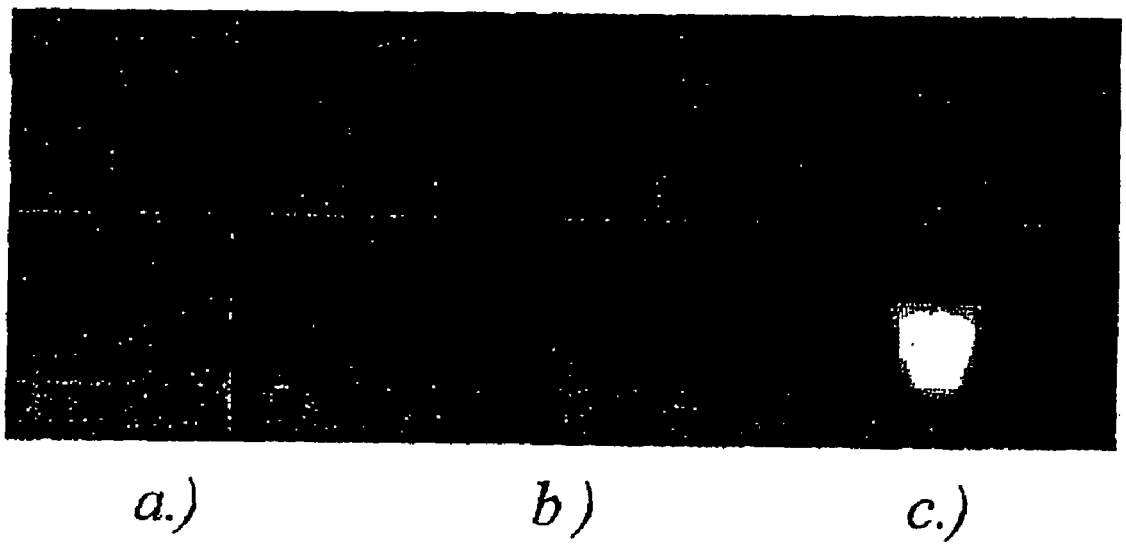

FIG. 3: Hela cells 1 hour after incubation with MEM (Minimal Essential Medium)
a) MEM alone (control)
b) MEM+Magnevist (100 pM)
c) MEM+ACGT (100 pM)

FIG. 4: Nucleic acid sequence of the C-myc$_{hum}$ DNA$_{Exon II}$ and the complete c-myc mRNA.

The exact location at which the ACGT is targeted (green) is shown. Exon I untranslated (blue hatched), Exon II translated (red), Exon III partially translated (red and blue hatched)

The following examples illustrate the invention.

DETAILED DESCRIPTION OF THE INVENTION

EXAMPLE 1

General Methods (A) Cell culture

Exponentially grown human HeLa-Cervix-Carcinoma-Cells and non-tumor cells (peripheral Lymphocytes) (DKFZ tumor bank) were cultivated in minimal essential medium (MEM culture medium, Sigma-Aldrich, Taufkirchen, Germany #8028) supplemented with 10% Fetal Bovine Serum (FBS, Sigma, Germany), 2 mM glutamine, 100 U/ml penicillin, 100 μg/ml streptomycin (Gibco Life Technologies, Karlsruhe, Germany). Cells were grown as monolayers in a mycoplasma free state as monitored by PCR (Mycoplasma PCR Primer Set; Stratagene Europe; Amsterdam, NL).

(B) Cell Growth Measurements

Cell growth measurements were performed by using a Coulter Counter ZM (Coulter Electronics Limited, Luton, England).

(C) Synthesis of Cys-[Antisense- or Random-Sequence]-Diethylenetriamine-pentaacetic Acid (DTPA)

To perform solid phase synthesis of peptide modules the Fmoc-strategy was used in a fully automated synthesizer Syro II (MultiSyn Tech, Witten, Germany). The synthesis was carried out on 0.05 mM Fmoc-As-TCP-resin (Trityl-Resin). The coupling agent used was 2-(1H-Benzoetriazole-1-yl)-1,1,3,3-tetramethyluronium hexafluorophosphate (HBTU). Side chain protecting groups were Lys(Boc), Cys(Trt) and Arg(Pbf). The protected peptidyl resin was treated with 20% Hexafluoroisopropanol in Dichloromethan for 5-10 minutes which in turn resulted in the fully protected peptide. In the first step, treatment with Diethylenetriamin was performed followed by a treatment with chloroacetic acid to form DTPA in the c-terminus of the peptide.

The protected peptidyl-DTPA was treated with 20% piperidin in dimethylformamide. Cleavage and deprotection of the peptide resin were effected by treatment with 90% trifluoroacetic acid, 5% ethanedithiol, 2.5% thioanisol, 2.5% phenol (v/v/v/v) for 2.5 hours at room temperature. All products were precipitated in ether and purified by preparative HPLC (Shimazu LC-8A, Duisburg, Germany) on a YMC ODS-A 7A S-7 μm reverse phase column (20×250 mm) using (a) 0.1% trifluroacetic acid (TFA) in water and (b) 60% acetonitrile in water as eluent. Peptides were removed with a successive linear gradient increasing from 25% B to 60% B in 40 min at a flow rate of 10 ml/min. The fractions corresponding to the purified conjugates were lyophilized. Sequences of single modules as well as the complete bimodular construct (Table. 1) were characterized with analytical HPLC (Shimadzu LC-10, Duisburg, Germany) and laser desorption mass spectrometry (Finnigan Vision 2000, Thermguest Analyt. Systeme, Egelsbach, Germany) yielding purification grades greater than 90%. The TPU transmembrane peptide (#3723; Table 1) and the AS/random PNA peptides (#153a/b; Table 1) were prepared in an identical procedure (Merrifield, J. Amer. Chem. Soc. 85: 2149-2154, 1963; Capino and Han, J. Org. Chem. 37: 3404-3409 (1972)).

(D) DTPH Gd-complex Formation

Stochiometric amounts of peptide-DTPA and $Gd^{3+}$ (Sigma-Aldrich, Germany, Cat. No. G7532) were solved in an aqueous NaCl-solution (0, 9%). After 12 hours the complexation process was stopped and purified as described in the previous section. The random PNA construct (#153b; Table 1) was prepared with an identical carrier conjugate.

(E) Fluorochrome Labeling

The $Gd^{3+}$-DTPH-Lys-Lys-[AS]-Cys-constructs (#153c; Table 1) were FITC-labeled only at the non-cleavable lysine-spacer site on the ε-amino group via usual peptide linkage during the first peptide synthesis.

(F) Peptide Purification

All products were precipitated in ether and purified by preparative HPLC (Shimazu LC-8A) on a YMC ODS-A 7A S-7 μm reverse phase column (20×250 mm) using of 0.1% trifluoroacetic acid in water (A) and 60% acetonitrile in water (B) as eluent. Peptides were eluted with a successive linear gradient increasing from 25% to 60% B-eluent in 49 min at a flow rate of 10 ml/min. The fractions corresponding to the purified conjugate were lyophilized. Sequences of single modules as well as the complete bimodulear construct are characterized with analytical HPLC (Shimadzu LC-10) and laser desorption mass spectrometry (Finnigan, Vision 2000).

(G) Antisense Conjugated Gadolinium Complex (ACGT)-Peptide Linkages

Cysteine groups of the human transmembrane peptide TPU [#3723; H$_2$N-KMTRQTWWH RIKHKC-(Cys-CO—NH$_2$)—(SH)—CONH$_2$; TPU (hum)] and the address peptide module Gd-compound {[AS/random] (#153a/153b; $Gd^{3+}$-DTPH—K—K—HN-(Cys-CO—NH$_2$)—(SH)—CONH$_2$; SV40-T-antigen)} (Table 1) were oxidized at the range of 2 mg/ml in a 20% DMSO water solution. 5 hours later the reaction was completed. The progress of oxidation was monitored by analytical C18 reverse phase HPLC.

(H) Localization of the ACGT

HeLa tumor cells plated on sterile, silan-coated glass slides embedded in quadriPERM plus (Heraeus, Osterode, Germany) and incubated for 24 h. After two wash-cycles with MEM culture medium, the cells were incubated with $Gd^{3+}$-DTPH-AS]-K$_2$-Cys-constructs (100 pM) at 37° C. in 5% $CO_2$ for 1 hour. Living cells were analysed by CLSM (Zeiss LSM 310, Oberkochem, Germany). The excitation line of an argon/krypton laser was used to detect fluorescence signal from FITC-labeled $Gd^{3+}$-DTPH-Lys-Lys-[AS]-K$_2$-Cys-constructs (#153c) (Table 1). To increase the contrast of optical sections, 12-20 single exposures were averaged. Parameters of the image acquisition were adapted to show signal intensities in accordance with the visual microscopic image.

(I) MR Imaging (a) Kinetic Studies: HeLa-cell-Uptake of the Gd-complex-transporter [without Address-sequence or with Either Antisense (ACGT)- or Random-sequence (RCGT)] Compared to Magnevist®.

Living HeLa-cells were harvested and divided into tubes (Falcon) (Cell No.: 20×10$^6$ cells per tube). The Gd-complex-transporter without address-sequence and the Magnevist® were each dissolved in MEM culture medium in a concentration of 100 pM and were then incubated for 10, 20, 30 and 60 minutes. After centrifugation of the tubes (800 rpm×10 min), the incubation medium (supernatant) was removed and the cells (pellet) were washed twice with culture medium without conjugates to remove all unbound $Gd^{3+}$-DTPH (Magnevist®) and Gd-complex-transporter.

MR imaging used a 1.5-T whole body Siemens "Magnetom Vision Plus" with a standard circular polarized head coil. The test tubes were firmly positioned parallel to each other totally submerged in a water bath. The imaging protocol consisted of a sagittal and coronar T1-weighted spin-echo-sequence (TR: 600 ms/TE:15 ms, scan time: 45 sec). The field of view (FOV) was 200 mm×200 mm, using an 256×256 imaging matrix and two acquisitions. Slice thickness was 2 mm resulting in a pixel size of 0.79 mm×0.78 mm. T1 and T2 relaxation-times within the pellets of both tubes were measured to evaluate the intracellular relaxivity of the respective contrast agents (R=1/T1). The T1-relaxation time was measured by means of an inversion-recovery-sequence (TR: 5000 ms/TE: 76 ms/TI: 25-4000 ms, 15 different TI-values, scan-time 15×25 sec, FOV: 160 mm×160 mm, Matrix: 132×256, slice thickness: 7 mm, pixel size: 1.21×0.63 mm). T2 relaxation-time was measured by a multi-echo-sequence (TR: 5000 ms/16 TE-values: 30 ms–245 ms, FOV: 250 mm×250 mm, Matrix: 256×256, slice thickness: 5 mm, pixel size: 0.98×0.98 mm, scan time: 21 min 21 sec). Signal-intensity measurements were obtained from HeLa cervix carcinoma cells and background. A tube with HeLa cells, incubated in MEM medium without contrast agent, was used as a control. In this way, the HeLa cells were additionally tested for uptake of the Gd-complex-transporter when bound to either a c-myc targeted AS-sequence (ACGT) or a random-sequence (RCGT).

(b) HeLa-cell-efflux of the ACGT

Due to a signal intensity maximum in lymphocytes and HeLa cells after a 60 minutes incubation time, it was decided to begin with efflux measurements after 1 hour. After this period, both cell types were washed with conjugate-free MEM culture medium in order to remove all Gd-complexes. This procedure was repeated hourly until no signal increase compared to the control tube (HeLa cells or lymphocytes in MEM medium without contrast agent) could be detected in T1 weighted sequences.

(c) Influx and Efflux of the ACGT and RCGT (Random-Sequence-conjugated-Gadolinium-Transporter) in Lymphocytes In order to test whether it is possible to differentiate between tumor and non-tumor cells in MRI using antisense, the same uptake and efflux experiments as performed with HeLa cells were conducted using lymphocytes.

EXAMPLE 2

The Conjugate of the Present Invention is Useful for Cellular Imaging and can Discriminate Between Tumor- and Non-tumor Cells There were two primary aims in these experiments: Firstly, to achieve a rapid and high accumulation of Gadolinium within the cell by means of a transporter of human origin and, secondly, to achieve a high degree of cell-specificity between targeted and non-targeted cells.

In pursuit of the first objective, it was attempted in a recent study to achieve an intracellular accumulation of gadolinium by application of high extracellular gadolinium-complex concentrations (1-25 mg/ml) resulting in an intracellular gadolinium-complex accumulation detectable by mass spectrometry methods peaking at 100 hours. However, time and concentration of the drug make a successful application of this method in vivo highly unlikely.

This result reinforced the need for rapid transport across the cell membrane as a decisive factor in in vivo molecular imaging. A plasma-membrane-translocation-peptide was reported in 1997 which was derived from a viral HIV-1 tat protein and possessed nuclear-import characteristics. Two years later, this truncated HIV-1 tat protein was used to accumulate iron and Gadolinium-complexes inside the cell. In this way, the Gadolinium-complexes could even be detected within the nucleus after incubation. However the HIV-1 tat peptide possesses a transactivating effect on the LTR (Long Terminal Repeat)-promotor. Due to these transactivating effects of HIV-1 tat peptide which might also activate intracellular promoters, for the present study a different method was choosen and human transport-peptide-units which show a comparable transport efficiency were examined.

Figure 1A:
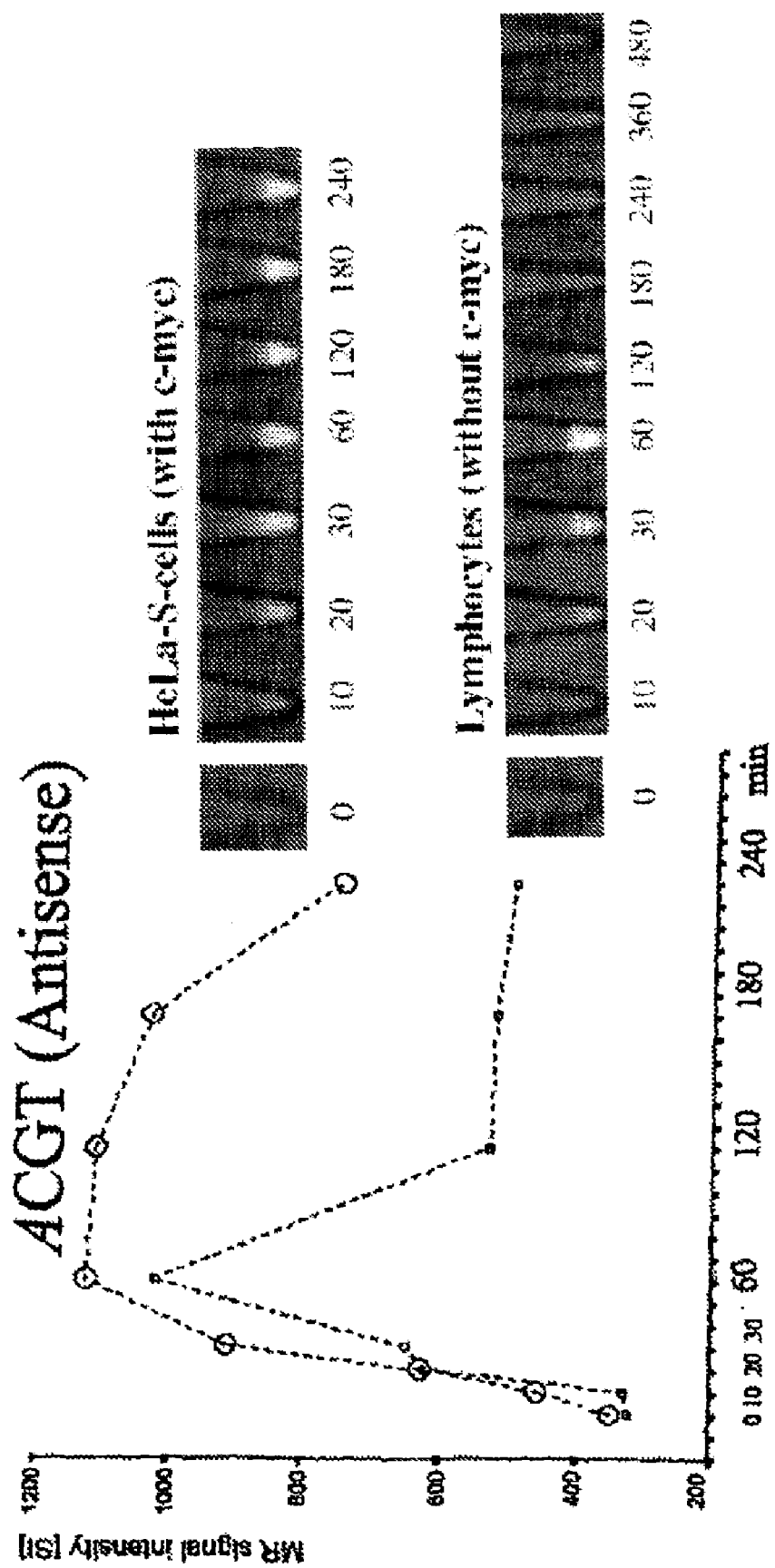
FIG. 1: Graph of MR signal intensity versus time for HeLa-cells and lymphocytes with
(a) ACGT (specific antisense);
(b) RCGT (random sequence)

Therefore, the choice for this study was to use a gadolinium-transporter-complex of human origin (Table 1). An increased intracellular signal intensity in tumor cells and lymphocytes could be detected after just 10 minutes incubation with the human gadolinium-complex transporter and subsequently a maximum after 1 hour could be achieved (whole body 1,5 T Siemens Magnetom, standard circular polarized head coil) (FIGS. 1a and b). This result was confirmed using confocal laser scanning microscopy (#153c) (CLSM) (FIG. 2). There was no signal detected in the nucleus which would suggest that the ACGT accumulated mainly in the cytoplasm (FIG. 2). If, by way of comparison, Magnevist® alone was used as a contrast agent, there was no signal change above that of the HeLa cells that had been incubated solely in MEM (FIG. 3). The measured relaxivity R within the HeLa-cell pellets changed by a factor of 3.17 after incubation with the gadolinium-complex transporter (R=0.000314) as compared to that after incubation solely with Magnevist® (R=0.000995).

Due to the lack of cell specificity of the viral HIV-1 tat peptide (no differentiation between tumor cells and normal surrounding tissue) high concentrations of this substance can be found in all cells. In the interest of the second objective, the cell-specificity, a different route was choosen by modifying the human gadolinium-complex transporter based on the differentiation between non-tumor and tumor cells as follows:

The c-myc-oncogene stimulates the G1/S transition of the cell-cycle by regulating the levels and activity of cyclins, cyclin-dependent kinases (cdk), cdk inhibitors and the pRb-binding transcription factor E2F. The E2F-pathway is deregulated in all tumors. This leads to a permanent upregulation of c-myc. The c-myc oncogene is characterized by three exons (FIG. 4). Exon I contains regulatory elements and will not be translated. Exon III will be partially translated, in contrast to the completely translated Exon II serving as the molecular target at the mRNA level in this study (translation initiation range) (FIG. 4). The ACGT is targeted at the c-myc-Exon II (FIG. 4). In normal, non-dividing cells, c-myc mRNA is hardly detectable. The antisense sequence of the ACGT binds to the c-myc mRNA in a stable manner. It is known that PNA-RNA-complexes possess a greater stability than DNA-RNA-complexes under physiological conditions. This suffices for the selection between c-myc-expressing and -lacking cells. Due to the retention of the ACGT solely in HeLa cells, the tumor cells can be clearly distinguished from normal cells in MRI. There was no observable difference in MRI in the influx of ACGT possessing the c-myc targeted AS-sequence between lymphocytes (non-tumor) and HeLa tumor cells (signal-intensity maximum after one hour).

Figure 1B:
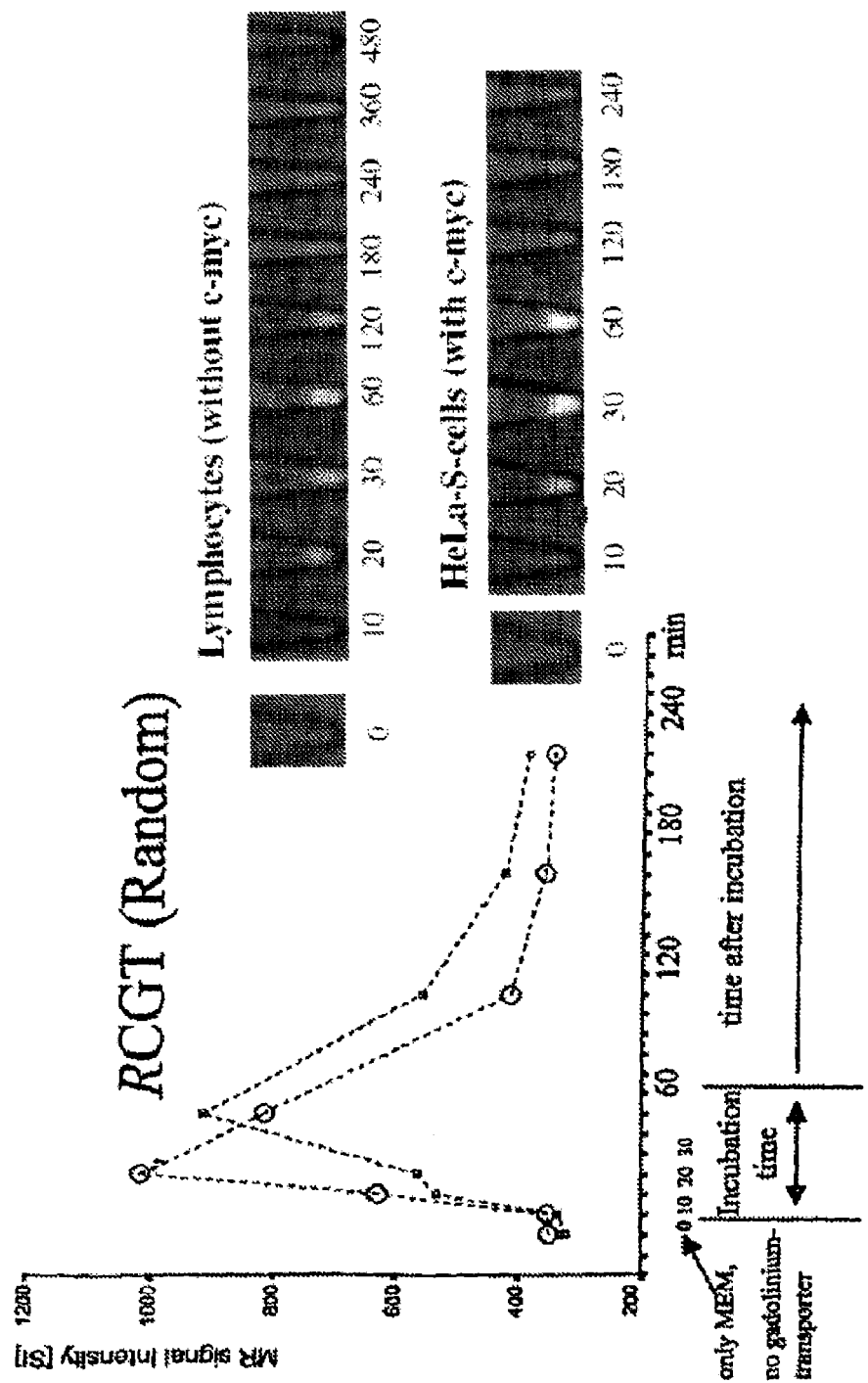

The signal-intensity in lymphocytes after a 2 hour incubation time had fallen by more than half from the previously attained maximum value because of the lack of c-myc mRNA in the cytoplasm to hybridize with the AS-sequence (FIG. 1a). In tumor cells (HeLa cells) on the other hand, the presence of c-myc mRNA allowed a hybridization with the c-myc targeted ACGT which then delayed the efflux of the Gd-complex, thus causing a significant relative signal enhancement in these tumor cells for approximately 3 hours (FIG. 1a). The random-sequence-conjugated-gadolinium-transporter (RCGT) could not hybridize with the c-myc-oncogene which resulted in an immediate efflux and a rapid decrease in signal intensity (FIG. 1b). Under these conditions apoptosis was not observed.

These results show that the conjugate of the present invention is useful in specific, non-invasive and side-effect-free diagnostic methods, e.g., for the molecular imaging of tumors, for example, follow-up's in tumor therapy. It would also seem to allow a clearer differentiation of tumor from healthy surrounding tissue in intraoperative MRI in neurosurgical procedures. Such intraoperative imaging is confronted with the problem of the surgical opening of the interstitial space which leads to the loss of interstitial contrast agent (Magnevist®). A clear distinction between tumor and surrounding tissue is then no longer possible. The ACGT of the present invention circumvents this problem and, thus, represents a promising solution. Additionally, the diagnostic conjugates of the present invention allow a better differentiation between tumor and fibrotic, edematous or inflamed tissue.

TABLE 1

Biochemical design of the functional modules used in the MRI study of Example 2.

| Prod. No. | Module | scheme | Sequences |
|---|---|---|---|
| #3723 | Transport-peptide | TPU (human) | $H_2N$-KMTRQTWWHRIKHKC-(Cys-CO—NH2)—(SH)—$CONH_2$** |
| #3724 | // | // | $H_2N$-MTRQTFWHRIKHKC-(Cys-CO—NH2)—(SH)—$CONH_2$ |
| #3725 | // | // | $H_2N$-KHKIRHWFTQRTMC-(Cys-CO—NH2)—(SH)—$CON_2$ |
| AC X00364 | Myc Gene DNA range Exon II | c-myc (DNA) | 5'... $_{4521}$ATGCCCCTCA ACGTTAGCTT$_{4540}$ ... 3' |
| mRNA | Myc mRNA range Exon II | c-myc (mRNA) | 5'...TACGGGGAGTTGCAATCGAA...3' ................... ................... ................... |
| #12a | Antisense | AS-PNA | $H_2N$-ATGCCCCTCAACGTTAGCTT-(Cys-CO—$NH_2$)—(SH)—$CONH_2$** |
| #12b | Random | RD-PNA. | $H_2N$-GCCTAGACAATCTGCTATAG-(Cys-CO—$NH_2$)—(SH)—$CONH_2$ |
| #153a | ACGT | $Gd^{3+}$-DTPH | $Gd^{3+}[DTPH]_4$-HN-$K_2$-AS-C-S^S-C-TPU |
| #153b | RCGT | $Gd^{3+}$-DTPH | $Gd^{3+}[DTPH]_4$-HN-$K_2$-RD-C-S^S-C-TPU |
| #153c | ACGT-FITC | $Gd^{3+}$-DTPH-FITC | $Gd^{3+}[DTPH]_4$-HN-$K^{FITC}$-K-AS-C-S^S-C-TPU |

153a Antisense-Sequence-Conjugated-Gadolinium-Transporter
153b Random-Sequence-Conjugated-Gadolinium-Transporter
153c ACGT for CLSM
S^S Cleavable spacer
** Single letter amino acid code
ACX00364 Accession number SRS data base

The invention claimed is:

1. A diagnostic conjugate having the structure: transmembrane module (TPU) coupled via a spacer to an address module (AS) coupled via a spacer to a signalling module (SM); wherein the transmembrane module is a cell-penetrating human transmembrane peptide comprising the amino acid sequence KMTRQTWWHRIKHKC (SEQ ID NO: 2), MTRQTFWHRIKHKC (SEQ ID NO: 3) or KHKIRHWFTQRTMC (SEQ ID NO: 4), the address module is a peptide nucleic acid (PNA) antisense to and hybridizing with a mRNA selected from the group consisting of c-myc-, c-ras-, hern-, sst1, or sst2-mRNA, and the signalling module is a compound trapping Gadolinium.

2. The diagnostic conjugate of claim 1, wherein the peptide nucleic acid (PNA) comprises the sequence H$_2$N-ATGC-CCCTCAACGTTAGCTT-COOH (SEQ ID NO: 5).

3. The diagnostic conjugate of claim 1, wherein the transmembrane module (TPU) is coupled to the address module (AS) via a covalently cleavable spacer I or the address module (AS) is coupled to the signalling module (SM) via a covalently non-cleavable spacer II.

4. The diagnostic conjugate of claim 3, wherein spacer I or spacer II comprises polylysine or polyglycine.

5. The diagnostic conjugate of claim 4, wherein spacer II carries a FITC-label.

6. The diagnostic conjugate of claim 1 having the following structure: transmembrane module (TPU)—spacer I comprising a cleavable disulfide bridge—address module (AS)—spacer II—signalling module (SM).

7. A diagnostic composition containing a diagnostic conjugate of claim 1.

8. A diagnostic composition containing a diagnostic conjugate of claim 6.

9. A diagnostic conjugate having the structure: transmembrane module (TPU) coupled via a cleavable spacer I to an address module (AS) coupled via a spacer II to a signalling module (SM); wherein the transmembrane module (TPU) is a cell-penetrating human transmembrane peptide comprising the amino acid sequence KMTRQTWWHRIKHKC (SEQ ID NO: 2), MTRQTFWHRIKHKC (SEQ ID NO: 3) or KHKIRHWFTQRTMC (SEQ ID NO: 4), the address module (AS) is a peptide nucleic acid (PNA) antisense to and hybridizing with a mRNA selected from the group consisting of c-myc-, c-ras-, hern-, sst1, or sst2-mRNA, and the signalling module (SM) is diethylenetriaminetriamine-pentaaceticacid acid (DTPA).

10. The diagnostic conjugate of claim 9, wherein the peptide nucleic acid (PNA) comprises the sequence H$_2$N-ATGC-CCCTCAACGTTAGCTT-COOH (SEQ ID NO: 5).

11. The diagnostic conjugate of claim 10, wherein the address module (AS) is coupled via a covalently cleavable spacer I to the transmembrane module (TPU) or the address module (AS) is coupled to the diethylenetriaminetriamine-pentaaceticacid acid (DTPA) via a covalently non-cleavable spacer II.

12. The diagnostic conjugate of claim 10, wherein spacer I comprises a cleavable disulfide bridge.

13. The diagnostic conjugate of claim 10, wherein spacer I or spacer II comprises polylysine or polyglycine.

14. The diagnostic conjugate of claim 11 wherein spacer II carries an FITC-label.

15. A diagnostic composition containing a diagnostic conjugate of claim 10 and pharmaceutically acceptable carrier.

16. The diagnostic conjugate of claim 1, wherein the compound trapping Gandolium is diethylenetriaminetriamine-pentaaceticacid acid (DTPA).

* * * * *

SEQUENCE LISTING

<160> NUMBER OF SEQ ID NOS: 7

<210> SEQ ID NO 1
<211> LENGTH: 1020
<212> TYPE: DNA
<213> ORGANISM: Homo sapiens

<400> SEQUENCE: 1

```
tttaggggat agctctgcaa ggggagaggt tcgggactgt ggcgcgcact gcgcgctgcg      60
ccaggtttcc gcaccaagac ccctttaact caagactgcc tcccgctttg tgtgccccgc     120
tccagcagcc tcccgcgacg atgcccctca acgttagctt caccaacagg aactatgacc     180
tcgactacga ctcggtgcag ccgtatttct actgcgacga ggaggagaac ttctaccagc     240
agcagcagca gagcgagctg cagccccgg cgcccagcga ggatatctgg aagaaattcg     300
agctgctgcc caccccgccc ctgtcccta gccgccgctc cgggctctgc tcgcctcct      360 acgttgcggt cacaccttc tcccttcggg gagacaacga cggcggtggc gggagcttct     420
ccacggccga ccagctggag atggtgaccg agctgctggg aggagacatg gtgaaccaga    480
```

-continued

```
gtttcatctg cgacccggac gacgagacct tcatcaaaaa catcatcatc caggactgta    540
tgtggagcgg cttctcggcc gccgccaagc tcgtctcaga gaagctggcc tcctaccagg    600
ctgcgcgcaa agacagcggc agcccgaacc ccgcccgcgg ccacagcgtc tgctccacct    660
ccagcttgta cctgcaggat ctgagcgccg ccgcctcaga gtgcatcgac ccctcggtgg    720
tcttccccta ccctctcaac gacagcagct cgcccaagtc ctgcgcctcg caagactcca    780
gcgccttctc tccgtcctcg gattctctgc tctcctcgac ggagtcctcc ccgcagggca    840
gccccgagcc cctggtgctc catgaggaga caccgcccac caccagcagc gactctggta    900
agcgaagccc gcccaggcct gtcaaaagtg ggcggctgga tacctttccc attttcattg    960
gcagcttatt taacgggcca ctcttattag gaaggagaga tagcagatct ggagagattt    1020
```

<210> SEQ ID NO 2
<211> LENGTH: 15
<212> TYPE: PRT
<213> ORGANISM: Artificial Sequence
<220> FEATURE:
<223> OTHER INFORMATION: Synthetic Construct

<400> SEQUENCE: 2

Lys Met Thr Arg Gln Thr Trp Trp His Arg Ile Lys His Lys Cys
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: Synthetic construct

<400> SEQUENCE: 3

Met Thr Arg Gln Thr Phe Trp His Arg Ile Lys His Lys Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic Construct

<400> SEQUENCE: 4

Lys His Lys Ile Arg His Trp Phe Thr Gln Arg Thr Met Cys
1               5                   10

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5 atgccccctca acgttagctt                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6

```
tacggggagt tgcaatcgaa                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
gcctagacaa tctgctatag                                                   20
```